United States Patent
Baskerville et al.

(10) Patent No.: US 10,271,777 B2
(45) Date of Patent: Apr. 30, 2019

(54) SYSTEM AND METHOD FOR BIOMETRIC ECG VERIFICATION OF PATIENT IDENTITY

(71) Applicant: Medicomp, Inc., Melbourne, FL (US)

(72) Inventors: Scott Baskerville, Melbourne Beach, FL (US); Sara England, Melbourne, FL (US)

(73) Assignee: Medicomp, Inc., Melbourne, FL (US)

( * ) Notice: Subject to any disclaimer, the term of this patent is extended or adjusted under 35 U.S.C. 154(b) by 0 days.

(21) Appl. No.: 15/755,388

(22) PCT Filed: Aug. 26, 2016

(86) PCT No.: PCT/US2016/049026
§ 371 (c)(1),
(2) Date: Feb. 26, 2018

(87) PCT Pub. No.: WO2017/035481
PCT Pub. Date: Mar. 2, 2017

(65) Prior Publication Data
US 2018/0249930 A1    Sep. 6, 2018

Related U.S. Application Data

(60) Provisional application No. 62/210,179, filed on Aug. 26, 2015.

(51) Int. Cl.
*A61B 5/117* (2016.01)
*A61B 5/00* (2006.01)
(Continued)

(52) U.S. Cl.
CPC ............ *A61B 5/117* (2013.01); *A61B 5/0006* (2013.01); *A61B 5/0245* (2013.01);
(Continued)

(58) Field of Classification Search
CPC ..... A61B 5/117; A61B 5/0006; A61B 5/0245; A61B 5/04525; A61B 5/0456; G06F 17/18
(Continued)

(56) References Cited

U.S. PATENT DOCUMENTS 6,993,378 B2    1/2006   Wiederhold et al.
8,100,835 B2    1/2012   Baruch
(Continued)

FOREIGN PATENT DOCUMENTS

WO    WO-2012140559 A1 * 10/2012 ............. A61B 5/681

*Primary Examiner* — John A Tweel, Jr.
(74) *Attorney, Agent, or Firm* — Mark Malek; Kelly G. Swartz; Widerman Malek, PL

(57) ABSTRACT

A system and method for verifying patient identity including a heart monitor, a memory, and a processor. The heart monitor may be adapted to collect a baseline ECG signal from a patient and a monitored ECG signal from the patient. The memory may be in electrical communication with the heart monitor and adapted to store a plurality of baseline statistical characteristics of the baseline ECG signal and a plurality of monitored statistical characteristics of the monitored ECG signal. The processor may be in electrical communication with the memory and adapted to compare the plurality of baseline statistical characteristics to the plurality of monitored statistical characteristics and determine a likelihood of patient match. The heart monitor may be configured for further collection of the monitored ECG signal if the likelihood of patient match is greater than a threshold level.

18 Claims, 4 Drawing Sheets

(51) Int. Cl.
*A61B 5/0245* (2006.01)
*A61B 5/0452* (2006.01)
*A61B 5/0456* (2006.01)
*G06F 17/18* (2006.01)

(52) U.S. Cl.
CPC .......... *A61B 5/0452* (2013.01); *A61B 5/0456* (2013.01); *A61B 5/04525* (2013.01); *G06F 17/18* (2013.01)

(58) Field of Classification Search
USPC ....................................................... 340/5.82
See application file for complete search history.

(56) References Cited

U.S. PATENT DOCUMENTS

| | | |
|---|---|---|
| 8,983,587 B2 | 3/2015 | Kurzweil et al. |
| 9,020,583 B2 | 4/2015 | Zhang |
| 9,031,288 B2 * | 5/2015 | Codella ................ A61B 5/1171 382/115 |
| 9,047,510 B2 * | 6/2015 | McLaughlin ........ G06K 9/0053 |
| 9,411,936 B2 * | 8/2016 | Landrum ............. A61B 5/0006 |
| 2014/0276156 A1 | 9/2014 | Zhang |

\* cited by examiner

SYSTEM AND METHOD FOR BIOMETRIC ECG VERIFICATION OF PATIENT IDENTITY

RELATED APPLICATIONS

This application claims the benefit under 35 U.S.C. § 119(a)-(d) of International Patent Application Serial No. PCT/US2016/49026 filed on Aug. 26, 2016 and titled System and Method for Biometric ECG Verification of Patient Identity, which claims the benefit under 35 U.S.C. § 119(e) of U.S. Provisional Patent Application Ser. No. 62/210,179 filed on Aug. 26, 2015 and titled System and Method for Biometric ECG Verification of Patient Identity, the entire content(s) of which is/are incorporated herein by reference

FIELD OF THE INVENTION

The present invention relates to the field of biometrics and, more specifically, to systems and methods for verifying identity of a patient using biometric indicia captured during electrocardiogram (ECG) monitoring.

BACKGROUND OF THE INVENTION

One or more biometric indicia, such as fingerprints, voiceprints, retinal scans and facial features, are often proposed to be used to identify, or to authenticate the asserted identity of a user who seeks access to a given resource. Approximately a dozen different biometric indicia have been proposed, but implementation methods for some of these approaches have not been disclosed. Many of these biometric indicia are associated with inherent physiological characteristics of the user's body. Another set of such indicia relate to what may be characterized as behavioral characteristics that partly reflect a learning or behavioral process and do not rely exclusively on purely physiological features. Use of one or more of these behavioral characteristics as a biometric indicium has received relatively little attention, in part because of the perceived difficulty of implementing a procedure to measure such a characteristic.

An example of a new physiological biometric feature is a sequence of bioelectric signals associated with cycles of the heart.

Cardiac muscle is myogenic and is capable of generating an action potential and depolarizing and repolarizing signals from within the muscle itself. An intrinsic conduction system (ICS), a group of specialized cardiac cells, passes an electrical signal throughout the heart. The ICS includes a sino-atrial (SA) node, an atrio-ventrical (AV) node, the bundle of His, right and left bundle branches, and the Purkinje fiber. These components spread the depolarization waves from the top (atria) of the heart down through the ventricles. The autonomic nervous system modulates the rhythm, rate and strength of cardiac contraction. When the cardiac muscle fibers contract, the volumes within the two atrial or two ventricle chambers are reduced and blood pressure increases. The (smaller) atrial chambers receive blood from the veins and pump the blood into the (larger) ventricle chambers, which pump blood out into the major arteries. The heart cycle normally begins in the right atrial chamber, and spreads to the left atrial chamber and then to the two ventricles. The atrial contraction is followed by the ventricular contraction in each cycle.

Simultaneous contraction of the large number of fibers in the ICS generates an electrical field that can be measured at the body surface using an electrocardiograph (ECG). This electrical signal includes a sequence of PQRST complexes. Most PQRST sequences are not uniform. The time interval between two consecutive R signal peaks, referred to as an R-R interval, corresponds to a heart pulse, with a rate that normally lies in a range of 60-90 beats per minute (bpm). The P signal corresponds to atrial depolarization (right side, followed by left side). The larger QRS complex corresponds to depolarization of the ventricles and repolarization of the atria; and the T signal corresponds to repolarization of the ventricles. A weaker U signal occasionally appears on the chart, representing remnants of ventricular repolarization.

A "wave" comprises a curve covering at least one complete component (P, Q, R, S and/or T). According to naming conventions accepted by most cardiology professionals, a time increment with a straight line amplitude extending between two consecutive signals, for example, from the end of an S wave to the beginning of an immediately following T wave, is referred to as a "segment." A time increment that includes at least one wave, with a graph that is at least partly curved, for example, from the beginning of a Q wave to the end of an S wave, is referred to as an "interval." Herein, a "wave," such as a P wave, will refer to the curvilinear graph (only) portion of a time interval, not including the associated time segment.

A P-Q time interval, normally of length $\Delta t(p-q) \approx 120\text{-}200$ msec, represents conduction time from initiation of atrial repolarization until initiation of ventricular depolarization, which is conventionally measured from the start of the P wave to the start of the Q wave.

Where the ICS is diseased or is affected by presence of Digitalis, the P-Q time interval may lengthen as the pulse rate decreases; a prolonged P-Q interval, substantially beyond 200 msec in length, is often evidence of atrio-ventricular block. An abnormally short P-Q interval, substantially below 120 msec in length, is often associated with hypertension and/or with paroxysms of tachycardia. The P-Q interval can also be shortened where the impulse originates in the AV node, or other atrial locations, rather than in the SA node.

The QRS time interval, normally of temporal length $\Delta t(q-t)$ z, 50-100 msec, represents conduction time from initiation of ventricular depolarization until the end of ventricular depolarization, and includes spread of the electrical impulse through the ventricular muscle. The P wave signal is normally gently rounded, not pointed or notched, and has a temporal length between about 50-110 msec. One or more of the P, Q, R, S and/or T peaks may be inverted in FIG. 2, depending upon electrode placement. A QRS interval greater than about 120 msec in temporal length often indicates ventricular arrhythmia or a block of one of the bundles.

Normally, an S-T segment amplitude is approximately equal to a P-Q segment amplitude. The amplitude of the S-T segment, relative to the baseline (e.g., elevated or depressed), and the shape of the T signal are often of interest. The T signal is normally rounded and slightly asymmetrical. Presence of a sharply pointed or grossly notched T signal may indicate presence of myocardial infarction (pointed segment) or of pericarditis (notched segment).

In some subjects, a beat (a single PQRST cycle) is sometimes missed. This arises from the particular physiology of that subject and has not (yet) been shown to arise unambiguously from the presence of high stress in that subject.

In normal ECG practice, ten or more electrodes including a ground electrode, are attached to the subject at selected, spaced apart locations. A chart of each PQRST cycle is printed separately on a 1 mm×1 mm grid, with 1 mm (horizontal) representing 40 msec (0.04 sec time increment) and 1 mm (vertical) representing 0.1 milliVolts (mV amplitude). An upper limit on amplitude is usually 20-30 mm (2-3 mV).

ECG analysis is generally limited to medical diagnostics and to comparison of shifts with the passage of time of ECG parameters of interest. No substantial work has been done applying the ECG results to other areas of interest, such as authentication of an asserted identity of a candidate-person, through analysis of selected ECG results to provide one or more physiologically based biometric indications associated with the candidate-person. Nor has any substantial use been made of evidence of a malady such as myocardial infarction or pericarditis as a characteristic for verifying the identity of a candidate-person.

What is needed is a method and associated system for measuring one or more (preferably several) statistical parameters associated with a PQRST cycle for a candidate person and authenticating, or declining to authenticate, the candidate-person's asserted identity with a reference person, using a comparison of the measured statistical parameter values (biometric indicia) with corresponding reference parameter values. Optionally, the comparisons should be cumulative so that the biometric indicia test can be made progressively more demanding, to minimize likelihood of commission of a type I error (positive result is false) and/or to balance the likelihoods of commission of a type I error and commission of a type II error (negative result is false) in these comparisons. These comparisons should also allow for possible changes with passage of time of PQRST cycle characteristics for a candidate-person. Preferably, evidence of presence of a malady in a reference person should be available for biometric use in comparison of a candidate person with this reference person.

SUMMARY OF THE INVENTION

With the above in mind, embodiments of the present invention are related to a system and method for verifying patient identity. The system may include a heart monitor, a memory, and a processor. The heart monitor may be adapted to collect a baseline ECG signal from a patient and a monitored ECG signal from the patient. The memory may be in electrical communication with the heart monitor and may be adapted to store a plurality of baseline statistical characteristics of the baseline ECG signal and a plurality of monitored statistical characteristics of the monitored ECG signal. The processor may be in electrical communication with the memory and adapted to compare the plurality of baseline statistical characteristics to the plurality of monitored statistical characteristics and determine a likelihood of patient match. The heart monitor may be configured to be enabled for further collection of the monitored ECG signal if the likelihood of patient match is greater than a threshold level.

The plurality of baseline statistical characteristics may be calculated by the processor based on one or more waveform characteristics of the baseline ECG signal.

The plurality of baseline statistical characteristics may include at least one of mean P-P interval, R-R interval, or T-T interval of the baseline ECG signal.

The plurality of baseline statistical characteristic may include a corresponding standard deviation of a mean interval of the baseline ECG signal.

The plurality of baseline statistical characteristics may include a mean R-T interval of the baseline ECG signal.

The plurality of baseline statistical characteristics may include a second mean interval in addition to the mean R-T interval. Between 30 and 50 percent of the likelihood of patient match may be determined by comparing the baseline mean R-T interval to a monitored mean R-T interval.

The threshold level may be configurable by a user.

The plurality of baseline statistical characteristics may be calculated based on one or more waveform characteristics of a plurality of cardiac cycles within the baseline ECG signal. The plurality of monitored statistical characteristics may be calculated based on one or more waveform characteristics of a plurality of cardiac cycles within the monitored ECG signal.

A mean of one or more of the monitored statistical characteristics may be utilized to determine the likelihood of patient match.

The monitor may be configured to be remotely enabled if the likelihood of patient match is lower than the threshold level.

The threshold level may be at least 50%.

The baseline statistical characteristics or the monitored statistical characteristics may be adjusted based on a monitored heart rate prior to determination of the likelihood of patient match.

The baseline statistical characteristics may be utilized to produce a curve of proportionality across a variable heart rate. The monitored statistical characteristics may be associated with a monitored heart rate and compared to the curve of proportionality at the value of the monitored heart rate to determine the likelihood of patient match.

The baseline ECG signal may be stored in the memory as a plurality of baseline peak arrays. Each of the plurality of baseline peak arrays may have a respective standard deviation and mean. The monitored ECG signal may be stored in the memory as a plurality of monitored peak arrays. Each of the plurality of monitored peak arrays may have a respective standard deviation and mean. Each of the plurality of baseline peak arrays may have a corresponding monitored peak array. The likelihood of patient match may be determined by comparing the mean of one or more of the monitored peak arrays to the mean of the corresponding baseline peak array.

A difference between the mean of one or more of the monitored peak arrays and the mean of the corresponding baseline peak array may be compared to a multiple of the standard deviation respective to the baseline peak array to determine the likelihood of patient match.

The method for verifying patient identity may include the steps of placing a heart monitor in electrical communication with the patient, collecting a baseline ECG signal from the patient utilizing a heart monitor, storing a plurality of baseline statistical characteristics of the baseline ECG signal in a memory in electrical communication with the heart monitor, collecting a monitored ECG signal utilizing the heart monitor, after a triggering event occurs, storing a plurality of monitored statistical characteristics of the monitored ECG signal in the memory, comparing the baseline statistical characteristics to the monitored statistical characteristics to determine a likelihood of patient match, using a processor in electrical communication with the memory, and enabling further collection of ECG signals by the heart monitor if the likelihood of patient match is greater than a threshold level.

The method may also include the steps of creating a curve of proportionality of the baseline statistical characteristics across a variable heart rate, associating the monitored statistical characteristics with a monitored heart rate, and comparing the curve of proportionality at the value of the monitored heart rate to the monitored statistical characteristic to determine the likelihood of patient match.

The method may further include the steps of storing the baseline ECG signal in the memory as a plurality of baseline peak arrays, determining respective standard deviation and mean values for each of the plurality of baseline peak arrays, storing the monitored ECG signal in the memory as a plurality of monitored peak arrays corresponding to the base line peak arrays, determining respective standard deviation and mean values for each of the plurality of baseline peak arrays, and comparing the mean of one or more of the monitored peak arrays to the mean of the corresponding peak array to determine the likelihood of patient match.

DETAILED DESCRIPTION OF THE INVENTION

Figure 1:
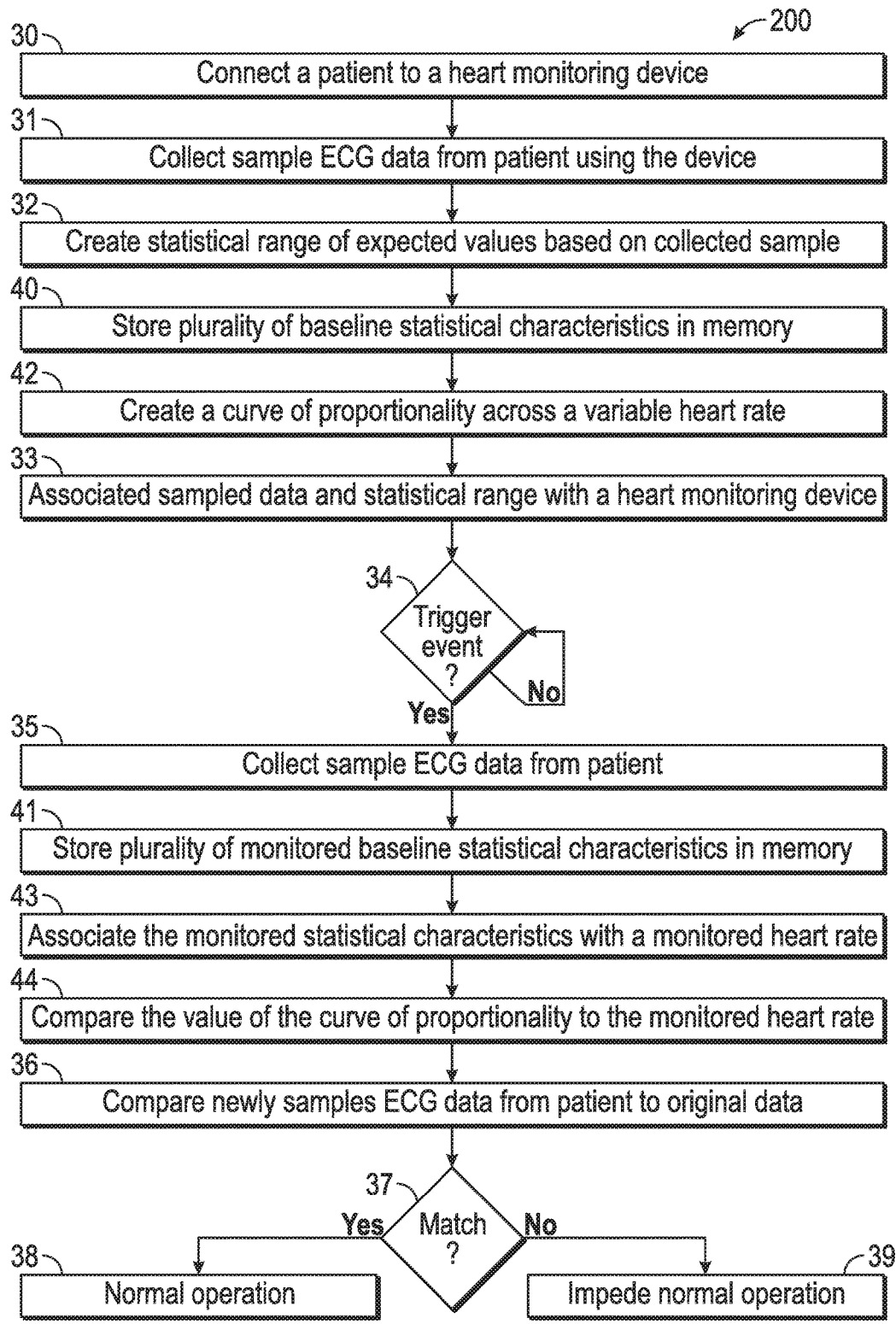
FIG. 1 is a flowchart of a method for biometric ECG verification of patient identity according to an embodiment of the present invention.
Figure 2:
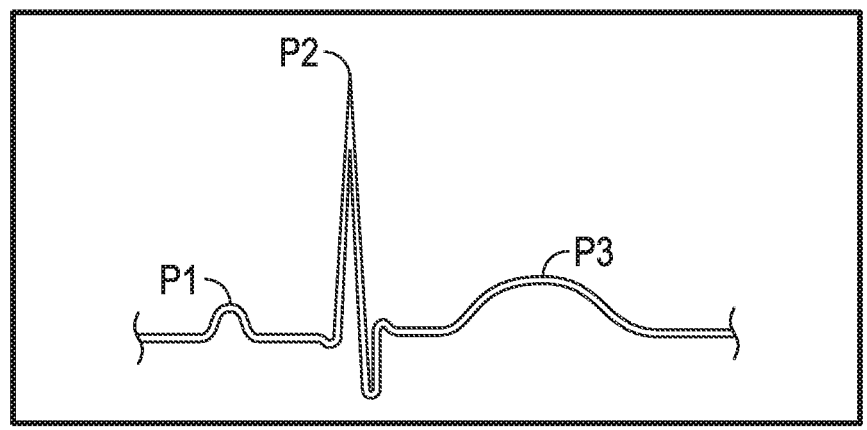
FIG. 2 is a depiction of an exemplary waveform that may be utilized by the inventive method for biometric ECG verification of patient identity according to an embodiment of the present invention.
Figure 3:
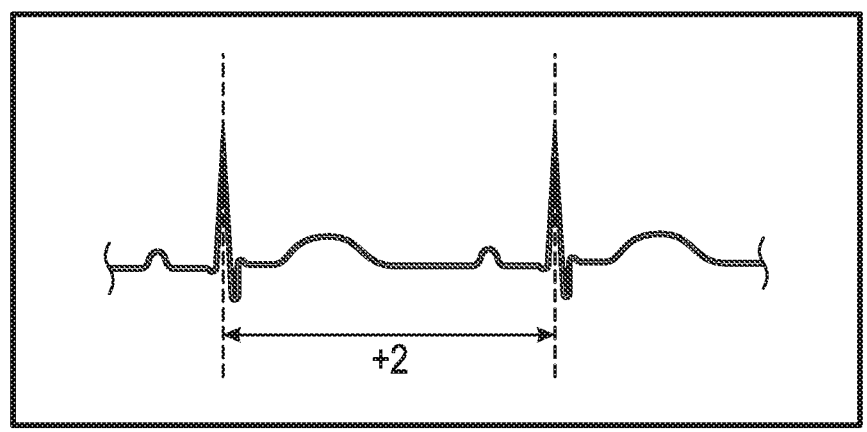
FIG. 3 is a depiction of an exemplary pair of waveforms depicting a R-R interval that may be utilized by the inventive method for biometric ECG verification of patient identity according to an embodiment of the present invention.
Figure 4:
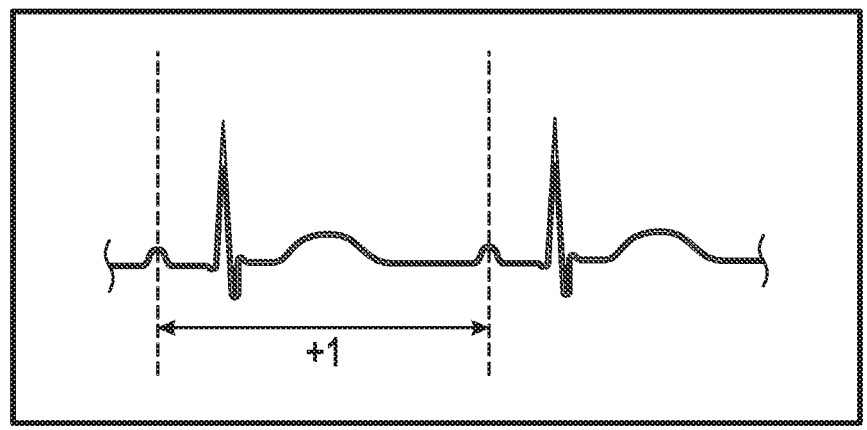
FIG. 4 is a depiction of an exemplary pair of waveforms depicting a P-P interval that may be utilized by the inventive method for biometric ECG verification of patient identity according to an embodiment of the present invention.
Figure 5:
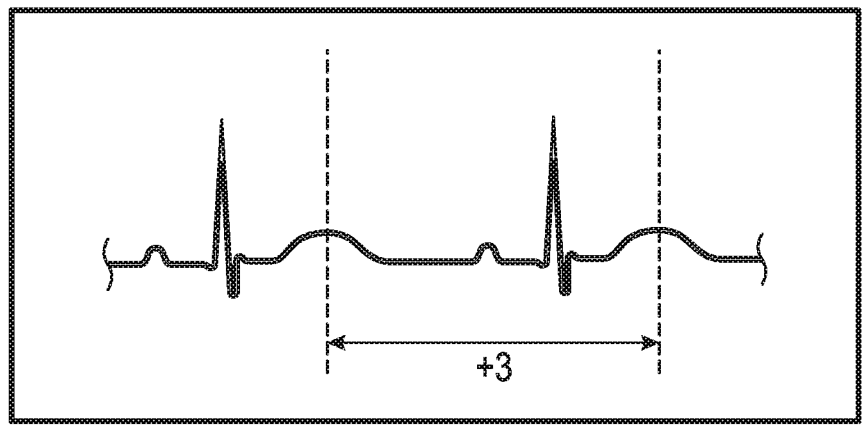
FIG. 5 is a depiction of an exemplary pair of waveforms depicting a T-T interval that may be utilized by the inventive method for biometric ECG verification of patient identity according to an embodiment of the present invention.
Figure 6:
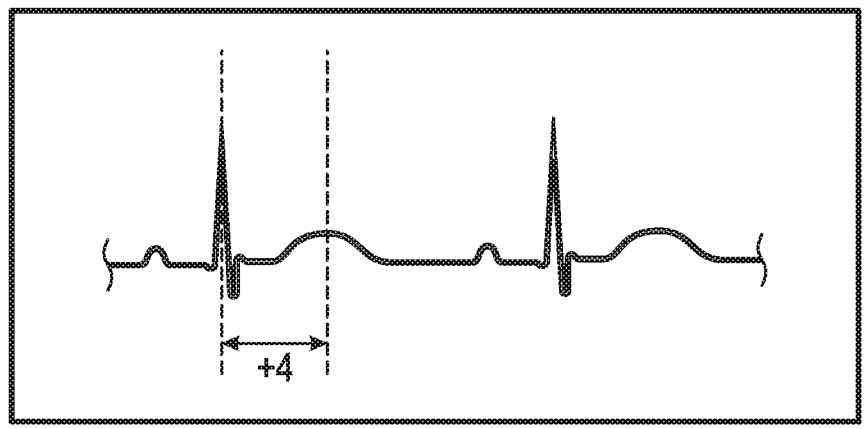
FIG. 6 is a depiction of an exemplary pair of waveforms depicting a R-T interval that may be utilized by the inventive method for biometric ECG verification of patient identity according to an embodiment of the present invention.

The present invention will now be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a system and method for collecting ECG signal data and biometrically identifying individuals via that data.

The system and method may include patients wearing heart monitors 101, or other monitoring devices, and analysis of ECG signal data collected by those heart monitors. The ultimate goal of the inventive system and method may be limiting cases of mistaken identity that potentially lead to the production of orphaned files and HIPAA violations.

The system 100 may include a heart monitor 101, or other device collecting patient information, which may house or be in electrical communication with a processor 103 and associated components, including, but not limited to, memory 102, power source, recording media, or the like. The system 100 may implement the inventive method of patient recognition.

As depicted in FIG. 1, the inventive method may include connecting a patient to an ECG monitor, or other heart monitoring device 30, sampling a patient's ECG signals 31, determining any necessary statistical characteristics of the sample 32, storing a plurality of baseline statistical characteristic in memory 40, creating a curve of proportionality across a variable heart rate 42, associating the sampled data and statistical characteristics with the device connected to the patient 33, waiting for a triggering event 34, collecting another sample of ECG data from the patient utilizing the device 35, storing a plurality of monitored baseline statistical characteristics in memory 41, associating the monitored statistical characteristics with a monitored heart rate 43, comparing the value of the curve of proportionality to the monitored heart rate 44, comparing subsequently gathered samples to the original sample 36, determining if there is a match 37, allowing normal operation of the monitoring device if there is a match 38, and impeding collection of further data if there is not a match 39. The method may then await another triggering event.

A patient may be properly identified and connected to an ECG monitor. Information from the ECG data signals obtained from the patient may be sampled by the system. By way of example, and not as a limitation, the patient's R-peak p2, P-peak p1, and T-peak p3 amplitudes may be measured. Again, by way of example, and not as a limitation, the patient's P-P interval t1, R-R interval t2, and T-T interval t3 may be measured. These measurements may be sampled from a number of successive or non-consecutive heartbeats. These samples, or measurements obtained from the samples, may be analyzed to determine any necessary statistical characteristics, including, but not limited to, standard deviations. The statistical characteristics may then be utilized to develop baseline biometrics of the identified patient from whom they were sampled. This baseline process may be done at the beginning of a given procedure and repeated only as necessary. By way of example, and not as a limitation, the baseline biometrics may include average R-peak, P-peak, or T-peak amplitudes and standard deviations. Again, by way of example, and not as a limitation, the baseline biometrics may include average P-P, R-R, or T-T intervals and standard deviations. The average values and standard deviations may be used to create a range of acceptable values, detection of which may result recognition of an identified user.

Different parameters may be weighted differently. By way of example, and not as a limitation, the R-T interval t4 may be given more weight than any other evaluated parameter. In one embodiment, the R-T interval t4 may account for 30% to 50% of the total decision to authenticate. The R-T interval t4 may preferably account for 40% of the total decision to authenticate. All other parameters may account for the remaining 70% to 50% of the decision to authenticate. All other parameters may preferably account for 60% of the decision to authenticate. That is, if the baseline R-T interval t4 matches the currently sampled R-T interval t4, there may be a 40% positive identification of the patient using the monitoring device. Measuring and matching additional baseline parameters may further increase the positive identification of the patient. The patient may be affirmatively verified at a predetermined percentage of positive identification. In one embodiment, a 50% to 100% positive identification may be required to allow for normal operation of the monitoring device.

After baseline biometrics are acquired, upon subsequent start-up of the monitoring device or upon the occurrence of other triggering events, the system may again sample data acquired from the patient's ECG data signals. This newly acquired ECG data may be compared with an existing baseline. If the newly sampled data fits within the individually calculated tolerance range for at least a minimum number of quantified characteristics, the system may allow for further operation of the monitoring system. After identifying the individual using the monitoring device as the same individual who provided the baseline data, the system may allow for the recording or transmission of ECG data. The ECG data may be transmitted to a remote monitoring center.

If the newly sampled data does not match the baseline biometrics within the required tolerance, the system may provide some notification either to the monitoring center or to the patient wearing the monitoring device. The tolerance for determining a match may be configurable. A single cardiac cycle may be utilized to determine whether there is a match. In some embodiments, multiple cardiac cycles may be utilized to determine whether there is a match. In one embodiment 1-100 cardiac cycles may be utilized to determine whether a match is present. A range of 1-30 cardiac cycles may be preferred. In some embodiments, multiple cardiac cycles may be averaged to determine if parameters match the baseline. Different parameters may be weighted evenly or unevenly. In embodiments in which parameters are weighted evenly, more than half of the parameters may be required to match in order to allow the monitoring device to operate normally. In embodiments in which parameters are weighted unevenly, more than 50% of the weighted value of parameters may be required to match in order for the monitoring device to operate normally. The specific parameters that are required to match and the weight given to each individual parameter may be configurable.

The notification of non-matching newly sampled data may consist of a warning to the monitoring center that the monitor being utilized by the patient may be on an unidentified, or unauthorized, patient. Such a notification may prevent ECG records from disparate patients from being comingled and may prevent related HIPAA violations. The system may display a warning to the user of the monitoring device, may try again to capture a matching sample, or may activate a "biometric lockout." Such a warning may instruct the user to contact the monitoring center. The monitoring center may verify the identity of the individual using the monitoring device. The system may allow for the "biometric lockout" to be remotely overridden if the patient has been identified as the correct user for the given monitor. This system or method may also be used in other products where implementation of biometric ECG analysis would be effective and convenient. The notification of non-matching newly sampled data may be provided to either the patient or a monitoring center on a visible display. Such a visible display may be an on-screen notification. In some applications of the inventive method, an alert or notification may be sent to first responders, property owners, or the like.

The inventive method may include statistical analysis of any component of a PQRST waveform. The P-P interval, R-R interval, T-T interval, P-wave amplitude, R-wave, amplitude, or T-wave amplitude may be acquired from the patient. Further analysis of other characteristics such as P-R interval, R-T interval t4, P-T interval, or the like may also be utilized. FIGS. 2-6 depict some exemplary characteristics that may be measured. Each of these components may be analyzed separately, each component measurement may be individually stored, averaged, or associated with its own respective set of desired statistical parameters, including, but not limited to standard deviation, variance, or the like.

The method for identifying the individual whose heart rate is being monitored may include comparing a newly acquired sample of one or more of these components to a stored sample of one or more of these components. The number of beats analyzed for each cycle may be a configurable value. Because each of the component measurements are individually stored and referenced, the verification method may be modified to include any combination of ECG signal features rather than the entire waveform.

The sampled data may be analyzed to develop a curve of proportionality factors versus heart rate. This curve may be stored as a look up table. The system may then determine the user's heart rate and utilize the look up table to determine the appropriate scaling factor. The scaling factor may be applied to the stored sample to allow it to be compared to the newly acquired sample. In another embodiment, the scaling factor may be applied to the newly acquired sample to allow it to be compared to the stored sample. If the newly acquired sample is within a statistically acceptable tolerance to the stored sample, the identity of the patient may be confirmed.

Figure 7:
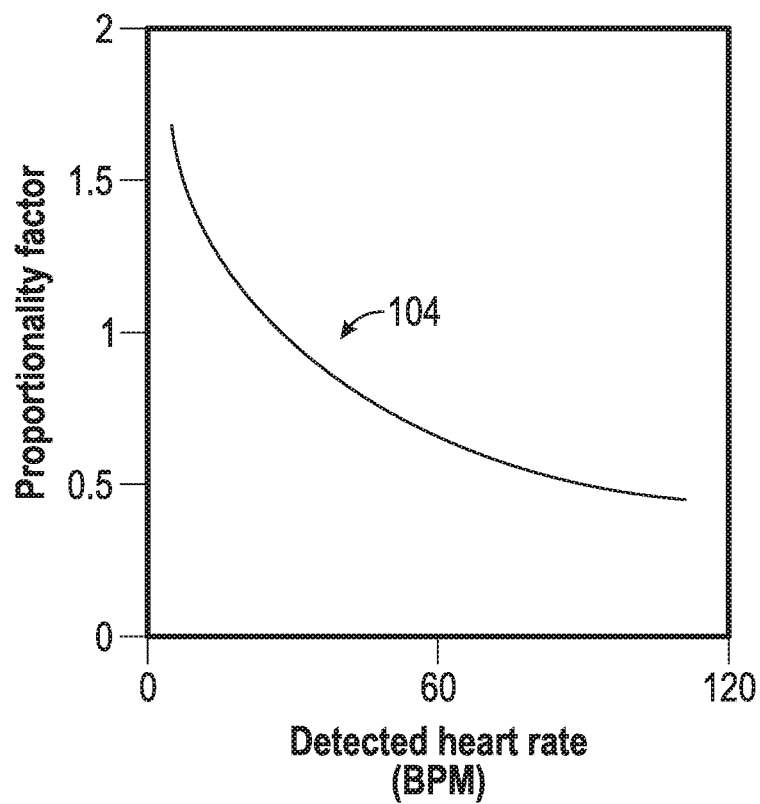
FIG. 7 is a plot of proportionality factor versus detected heart rate that may be utilized by the inventive method for biometric ECG verification of patient identity according to an embodiment of the present invention.
Figure 8:
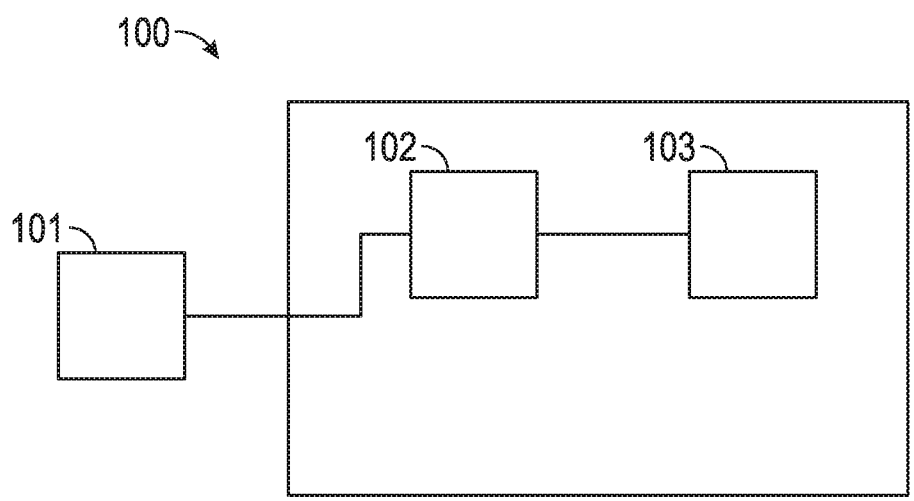
FIG. 8 is a block diagram of the system for verifying patient identity according to an embodiment of the invention.

The plot depicted in FIG. 7 is a graphical representation of what a lookup table may consist of in regards to the ECG wave morphology changes as a function of heart rate. The curve in this image represents a decaying exponential relationship; however, this curve could be any shape/scale depending on what is deemed appropriate and accurate on an application-by-application basis. The relationship can be established through a meta-data statistical analysis of heart rate-dependent morphology changes, or it can be calculated on an individual basis through evaluation of intracycle component measurements for different heart rates. Best-fit representations of collected data with a determined statistical significance may be developed for use in this system. The lookup system may account for shortening of time gaps in between different phases of the cardiac as the heart rate increases and lengthening of these gaps as heart rate decreases.

Once the curve or set of relationships is established, the heart rate may be measured or selected and the associated proportionality factor can be selected. If the baseline is established at 60 BPM, any heart rate detected or selected after the baseline is established may be compared to that value, which is associated with a proportionality factor of 1. Theoretically, heart rates higher than 60 would imply shortening of the time between atrial contraction and ventricular contraction (as an example), so some proportionality factor less than 1 would be multiplied by the established baseline P-R distance to ensure an appropriate adjustment is made. The opposite is true for heart rates slower than, for example, 60. The use of this concept may allow biometric algorithms to be more specific by having situation-specific and responsive tolerances, and it may allow simulation algorithms to be more biologically accurate.

As shown in FIG. 1, the inventive method may include collecting an ECG data sample from a patient 31. This data may be associated with a specific heart rate monitor device. The sampled data may be analyzed and recorded as the stored sample. A look up table may contain attributes of heart signal information associated with different heart rates. A trigger event may occur that requires the verification of the identity of the patient using the heart rate monitor. After the occurrence of the trigger event, which may be, but is not limited to, rebooting the heart monitoring device, passage of a specific amount of time, or a lapse in the collection of meaningful heart data, newly sampled ECG data may be collected by the heart rate monitoring device for a configured number of heart beats. The newly sampled data may be analyzed in preparation for comparing the newly sampled data to the stored sample. The look up table may be utilized when comparing subsequently acquired heart rate data to the initially acquired data.

The analysis may include sorting the collected waveform peaks into three arrays with lengths equal to the number of sampled heart beats. In one embodiment, the system may be configured to collect data from four heartbeats. In such a configuration, the collected waveform may be sorted into twelve separate peaks forming three arrays of four peaks each. In embodiments capturing five heartbeats, there may be three arrays of five peaks each. Arranging the individual peaks by amplitude from largest to smallest will place the R-signal peaks first, followed by the T-wave peaks, with the P-signal peaks last. The four R-signal peaks may for a first array. The four T-wave peaks may form a second array. The four P-signal peaks may form a third array. The amplitude of the peaks in each array may be averaged to create a mean amplitude along with a standard deviation. A tolerance range may be calculated for each array. The low end of the tolerance range may be the standard deviation subtracted from the mean. The high end of the tolerance range may be the standard deviation added to the mean. The number of standard deviations to include when calculated the range may be configurable. The standard deviations may be adjusted to tolerances to achieve acceptable reliability of the method. These measured amplitudes and standard deviations may be compared to subsequently acquired data to determine the percentage of similarity between the baseline and the subsequently acquired data. This may be done for either wave amplitude or wave distance. Upon comparing the subsequently acquired data, the system may provide an indication of whether or not the patient wearing the monitoring device is the same as the person originally associated with the monitoring device.

One potential benefit of this method may include the omission of P-wave measurements in a patient with atrial fibrillation. In patients with atrial fibrillation, the collection and analysis of P-wave measurements provide little value to, or may actually impede, the identification verification method.

This method may also include verification through the analysis of the aforementioned statistical parameters (i.e. using standard deviation of the P-wave-to-T-wave peak distance as a verification parameter).

This method may be performed with only one previously stored signal. This method may use only one measured parameter of one heart cycle to verify/deny the identity of a patient.

This method allows for an effective and useful updating of each individual component of a user's ECG signal. It has been shown that the morphology of an individual's ECG signal changes over time. Therefore, it is important to frequently update baseline data in accordance with newly verified signals. The method may create small statistical updates to sampled data over time. These updates may prevent the patient from being misidentified as an unidentified user due to normal morphology changes. Regular updates to stored data may allow for the device to evolve with the user's changing body over time.

In the field of cardiac telemetry, monitoring units are known to be improperly transferred from one patient to another. An increase in improper data handling or removal due to failure to return equipment for correct post-procedure processing has occurred. This system and method may serve as a line of defense against potential HIPAA violations arising from these improper transfers. The proposed system and method may reduce these violations and may be implemented in a way that prevents a significant percentage of orphaned files from being produced as well.

The implementation of this algorithm will help to reduce the number of cases in which heart monitors are sending patient data to the incorrect patient record, which can lead to HIPAA violations.

The system and method of ECG biometry identification techniques may be used in tandem with other biometric identifiers for security applications, including, but not limited to, building access, or the like.

In instances in which the biometric identification method cannot confirm the patient's identity, an alert system may be employed to alert the monitoring center or the patient so that the situation can be rectified.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the description of the invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

That which is claimed is:

1. A system for verifying patient identity comprising:
a heart monitor adapted to collect a baseline ECG signal from a patient and a monitored ECG signal from the patient;
a memory in electrical communication with the heart monitor and adapted to store a plurality of baseline statistical characteristics of the baseline ECG signal and a plurality of monitored statistical characteristics of the monitored ECG signal; and
a processor in electrical communication with the memory and adapted to compare the plurality of baseline statistical characteristics to the plurality of monitored statistical characteristics and determine a likelihood of patient match;
wherein the heart monitor is configured to be enabled for further collection of the monitored ECG signal if the likelihood of patient match is greater than a threshold level;
wherein the baseline ECG signal is stored in the memory as a plurality of baseline peak arrays;
wherein each of the plurality of baseline peak arrays has a respective standard deviation and mean;
wherein the monitored ECG signal is stored in the memory as a plurality of monitored peak arrays;
wherein each of the plurality of monitored peak arrays has a respective standard deviation and mean;
wherein each of the plurality of baseline peak arrays has a corresponding monitored peak array; and
wherein the likelihood of patient match is determined by comparing the mean of one or more of the monitored peak arrays to the mean of the corresponding baseline peak array.

2. The system according to claim 1 wherein the plurality of baseline statistical characteristics are calculated by the processor based on one or more waveform characteristics of the baseline ECG signal.

3. The system according to claim 1 wherein the plurality of baseline statistical characteristics include at least one of mean P-P interval, R-R interval, or T-T interval of the baseline ECG signal.

4. The system according to claim 1 wherein the plurality of baseline statistical characteristic include a corresponding standard deviation of a mean interval of the baseline ECG signal.

5. The system according to claim 1 wherein the plurality of baseline statistical characteristics include a mean R-T interval of the baseline ECG signal.

6. The system according to claim 5 wherein the plurality of baseline statistical characteristics include a second mean interval in addition to the mean R-T interval;
wherein between 30 and 50 percent of the likelihood of patient match is determined by comparing the baseline mean R-T interval to a monitored mean R-T interval.

7. The system according to claim 1 wherein the threshold level is configurable by a user.

8. The system according to claim 1 wherein the plurality of baseline statistical characteristics are calculated based on one or more waveform characteristics of a plurality of cardiac cycles within the baseline ECG signal; and
wherein the plurality of monitored statistical characteristics are calculated based on one or more waveform characteristics of a plurality of cardiac cycles within the monitored ECG signal.

9. The system according to claim 8 wherein a mean of one or more of the monitored statistical characteristics is utilized to determine the likelihood of patient match.

10. The system according to claim 1 wherein the monitor is configured to be remotely enabled if the likelihood of patient match is lower than the threshold level.

11. The system according to claim 1 wherein the threshold level is at least 50%.

12. The system according to claim 1 wherein the baseline statistical characteristics or the monitored statistical characteristics are adjusted based on a monitored heart rate prior to determination of the likelihood of patient match.

13. The system according to claim 1 wherein the baseline statistical characteristics are utilized to produce a curve of proportionality across a variable heart rate; and
wherein the monitored statistical characteristics are associated with a monitored heart rate and compared to the curve of proportionality at the value of the monitored heart rate to determine the likelihood of patient match.

14. The system according to claim 1 wherein a difference between the mean of one or more of the monitored peak arrays and the mean of the corresponding baseline peak array is compared to a multiple of the standard deviation respective to the baseline peak array to determine the likelihood of patient match.

15. A system for verifying patient identity comprising:
a heart monitor adapted to collect a baseline ECG signal from a patient and a monitored ECG signal from the patient;
a memory in electrical communication with the heart monitor and adapted to store a plurality of baseline statistical characteristics of the baseline ECG signal and a plurality of monitored statistical characteristics of the monitored ECG signal; and
a processor in electrical communication with the memory and adapted to compare the plurality of baseline statistical characteristics to the plurality of monitored statistical characteristics and determine a likelihood of patient match;
wherein the heart monitor is configured to be enabled for further collection of the monitored ECG signal if the likelihood of patient match is greater than a threshold level;
wherein the baseline statistical characteristics are utilized to produce a curve of proportionality across a variable heart rate; and
wherein the monitored statistical characteristics are associated with a monitored heart rate and compared to the curve of proportionality at the value of the monitored heart rate to determine the likelihood of patient match.

16. A method for verifying patient identity comprising the steps of:

placing a heart monitor in electrical communication with a patient;

collecting a baseline ECG signal from the patient utilizing the heart monitor;

storing a plurality of baseline statistical characteristics of the baseline ECG signal in a memory in electrical communication with the heart monitor;

collecting a monitored ECG signal utilizing the heart monitor, after a triggering event occurs;

storing a plurality of monitored statistical characteristics of the monitored ECG signal in the memory;

comparing the baseline statistical characteristics to the monitored statistical characteristics to determine a likelihood of patient match, using a processor in electrical communication with the memory;

enabling further collection of ECG signals by the heart monitor if the likelihood of patient match is greater than a threshold level;

creating a curve of proportionality of the baseline statistical characteristics across a variable heart rate;

associating the monitored statistical characteristics with a monitored heart rate; and comparing the curve of proportionality at the value of the monitored heart rate to the monitored statistical characteristic to determine the likelihood of patient match.

17. The method according to claim 16 wherein the plurality of baseline statistical characteristics includes at least one of mean P-P interval, R-R interval, or T-T interval and the mean R-T interval of the baseline ECG signal.

18. The method according to claim 16 further comprising the steps of:

storing the baseline ECG signal in the memory as a plurality of baseline peak arrays;

determining respective standard deviation and mean values for each of the plurality of baseline peak arrays;

storing the monitored ECG signal in the memory as a plurality of monitored peak arrays corresponding to the base line peak arrays;

determining respective standard deviation and mean values for each of the plurality of baseline peak arrays; and comparing the mean of one or more of the monitored peak arrays to the mean of the corresponding peak array to determine the likelihood of patient match.

* * * * *